US008859725B2

(12) United States Patent
Quintana Porras et al.

(10) Patent No.: US 8,859,725 B2
(45) Date of Patent: Oct. 14, 2014

(54) HEALTHY KIDNEY BIOMARKERS

(75) Inventors: Luis F. Quintana Porras, Barcelona (ES); Amanda Sole Gonzalez, Barcelona (ES); Elisenda Bañón-Maneus, Barcelona (ES); Josep M. Campistol, Barcelona (ES); Pedro Rodriguez Cutillas, London (GB)

(73) Assignees: Queen Mary and Westfield College, University of London, London (GB); Hospital Clinic I Provincial de Barcelona, Barcelona (ES); Institut de Investigacions Biomediques August PI I Sunyer, Barcelona (ES)

( * ) Notice: Subject to any disclaimer, the term of this patent is extended or adjusted under 35 U.S.C. 154(b) by 578 days.

(21) Appl. No.: 13/056,434

(22) PCT Filed: Jul. 31, 2008

(86) PCT No.: PCT/EP2008/060062
§ 371 (c)(1),
(2), (4) Date: Apr. 22, 2011

(87) PCT Pub. No.: WO2010/012306
PCT Pub. Date: Feb. 4, 2010

(65) Prior Publication Data
US 2011/0201518 A1 Aug. 18, 2011

(51) Int. Cl.
| | |
|---|---|
| *A61K 38/00* | (2006.01) |
| *C07K 5/00* | (2006.01) |
| *C07K 7/00* | (2006.01) |
| *C07K 16/00* | (2006.01) |
| *C07K 17/00* | (2006.01) |
| *C07K 1/00* | (2006.01) |
| *C07K 14/47* | (2006.01) |
| *C07K 7/18* | (2006.01) |
| *C07K 14/74* | (2006.01) |
| *G01N 33/68* | (2006.01) |

(52) U.S. Cl.
CPC ............ *G01N 33/6893* (2013.01); *C07K 14/47* (2013.01); *C07K 7/18* (2013.01); *C07K 14/70539* (2013.01); *G01N 2800/347* (2013.01); *G01N 33/6851* (2013.01); *G01N 2800/245* (2013.01)
USPC ............ 530/324; 530/326; 530/328; 530/344

(58) Field of Classification Search
None
See application file for complete search history.

(56) References Cited

FOREIGN PATENT DOCUMENTS

| | | | |
|---|---|---|---|
| JP | 2002125673 | | 5/2002 |
| WO | WO 2004/038377 | * | 5/2004 |
| WO | 2007000466 | | 1/2007 |
| WO | 2007104537 | | 9/2007 |
| WO | 2007121922 | | 11/2007 |

OTHER PUBLICATIONS

Serafini-Cessi et al. Tamm-Hosfall Glycoprotein: Bioloiy and Clinical Relevance. American Journal of Kidney Diseases. Oct. 2003. vol. 42, Nol. 4, pp. 658-676.*
Kirkpatrick et al. The absolute quantification strategy: a general procedure for the quantification of proteins and post-translational modifications. Methods, 2005, vol. 35, pp. 265-273.*
White et al. Improved hig-throughput mass spectrometry with concnetration and dessalting of peptide samples using PerfectPure® C-18 Tips and Resasech pro multi-channel pipette. Eppendorf BioNews Application Notes, Nov. 2004, accessed online Sep. 19, 2013 at http://www.eppendorf.com/script/cms-newspic.php?id=8286&col=DOWNLOADFILE , pp. 3-4.*
International Search Report dated Dec. 10, 2008, from the corresponding PCT/EP2008/060062.
Michael Jürgens et al.: "Towards Characterization of the Human Urinary Peptidome", Combinatorial Chemistry and High Throughput Screening, Hilversum, NL, vol. 8, No. 8, Dec. 1, 2005, pp. 757-765, XP008067432, ISSN: 1386-2073, p. 758-p. 759.
K. Kobayashi et al: "Conditions for Solubilization of Tamm-Horsfall Protein/Uromodulin in Human Urine and Establishment of a Sensitive and Accurate Enzyme-Linked Imunosorbent Assay (ELISA) Method" Archives of Biochemistry and Biophysics, vol. 388, No. 1, Apr. 1, 2001, pp. 113-120, XP002505365, ISSN: 0003-9861.
Stefan Schaub et al.: "Proteomic-Based Detection of Urine Proteins Associated with Acute Renal Allograft Rejection" Journal of the American Society of Nephrology, Williams and Wilkins, Baltimore, MD, US, vol. 15, No. 1, Jan. 1, 2004, pp. 219-227, XP002381566, ISSN: 1046-6673.
Georg Martin Fiedler et al: "Standardized Peptidome Profiling of Human Urine by Magnetic Bead Separation and Matrix-Assisted Laser Desorption/Ionization Time-of-Flight Mass Spectrometry", Clinical Chemistry, vol. 53, No. 3, Mar. 2007, pp. 421-428, XP002505366, ISSN: 0009-9147.
Harald Mischak et al: "High-Resolution Proteome/Peptidome Analysis of Peptides and Low-Molecular-Weight Proteins in Urine", Proteomics Clinical Applications, vol. 1, No. 8, Aug. 2007, pp. 792-804, XP002505367, ISSN: 1862-8346.
Hassan Dihazi et al: "Urinary Proteomics: A Tool to Discover Biomarkers of Kidney Diseases", Expert Rev. Proteomics 4(1), 39-50 (2007), 2007 Future Drugs Ltd., ISSN 1478-9450.

(Continued)

*Primary Examiner* — Marcela M Cordero Garcia
(74) *Attorney, Agent, or Firm* — Katten Muchin Rosenman LLP

(57) ABSTRACT

The invention provides novel healthy kidney biomarkers useful in the monitoring of renal function and in the prognosis and diagnosis of renal dysfunctions, especially those related to graft rejection. The invention further relates to methods for aiding in the evaluation, and design of personalized therapies in transplantation nephrology.

4 Claims, 5 Drawing Sheets

(56) References Cited

OTHER PUBLICATIONS

Hassan Dihazi et al: "Characterization of Diabetic Nephropathy by Urinary Proteomic Analysis: Identificaiton of a Processed Ubiquitin Form as a Differentially Excreted Protein in Diabetic Nephropathy Patients", Clinical Chemistry 53:9, 1636-1645 (2007).

F. O'Valle et al: "Poly(ADP-Ribose) Polymerase Expression in Kidney Transplantation: From Alfa ($\alpha$) to Omega ($\Omega$)", Elsevier, Transplantation Proceedings, 39, 2099-2101 (2007).

Stefan Schaub et al: "Proteomic-based Identification of Cleaved Urinary $\beta$ 2-microglobulin as a Potential Marker for Acute Tubular Injury in Renal Allografts", American Journal of Transplantation 2005; 5: 729-738, Blackwell Munksgaard.

W Peng et al: "Non-invasive Detection of Acute Renal Allograft Rejection by Measurement of Vascular Endothelial Growth Factor in Urine", The Journal of International Medical Research, 2007; 35: 442-449.

E. O'Riordan et al: "Characterization of Urinary Peptide Biomarkers of Acute Rejection in Renal Allografts", American Journal of Transplantation 2007; 7: 930-940, Blackwell Munksgaard.

Trairak Pisitkun, et al: "Identification and Proteomic Profiling of Exosomes in Human Urine", PNAS, Sep. 7, 2004, vol. 101, No. 36, 13368-13373.

John R. Hoyer et al.: "Pathophysiology of Tamm-Horsfall Protein", Kidney International, vol. 16 (1979), 279-289.

Theodor Mindroiu et al: "Identification of a New Kinin in Human Urine", The Journal of Biological Chemistry, vol. 261, No. 16, Issue of Jun. 5, 1986, 7407-7411.

F.K. Stevenson et al: "Subunits of Tamm-Horsfall Glycoprotein", Biochem. J. (1970) 116, 791-796.

Michael J. Rindler et al: "Uromodulin (Tamm-Horsfall Glycoprotein/Uromucoid) Is a Phosphatidylinositol-linked Membrane Protein", The Journal of Biological Chemistry, vol. 265, No. 34, Issue of Dec. 5, 1990, 20784-20789.

* cited by examiner

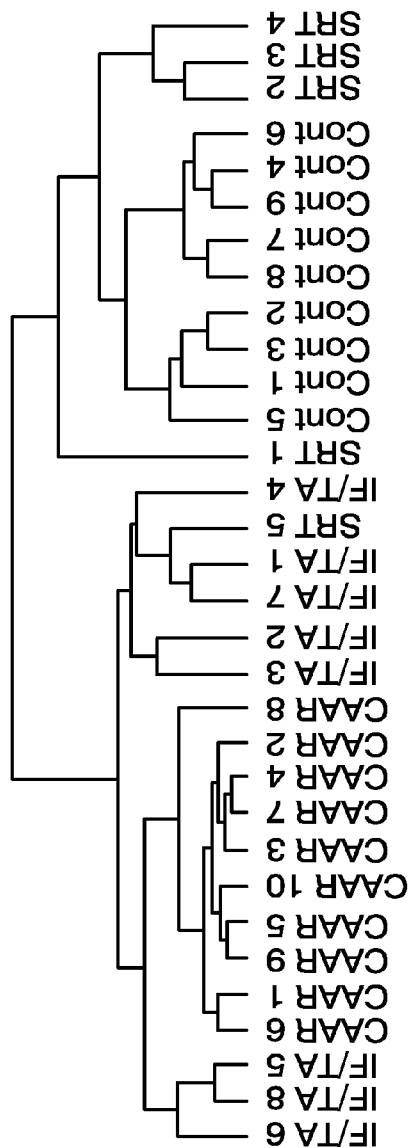
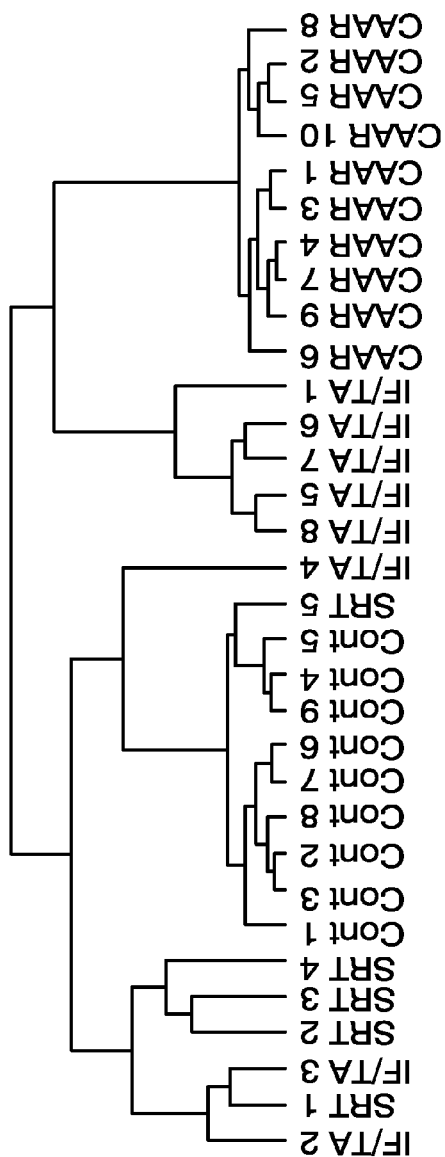
FIG. 2A
FIG. 2B

SEQUENCE LISTING

<160> NUMBER OF SEQ ID NOS: 10

<210> SEQ ID NO 1
<211> LENGTH: 15
<212> TYPE: PRT
<213> ORGANISM: Homo sapiens

<400> SEQUENCE: 1

Ile Asp Gln Ser Arg Val Leu Asn Leu Gly Pro Ile Thr Arg Lys
1               5                   10                  15

<210> SEQ ID NO 2
<211> LENGTH: 17
<212> TYPE: PRT
<213> ORGANISM: Homo sapiens

<400> SEQUENCE: 2

Gln Pro Met Val Ser Ala Leu Asn Ile Arg Val Gly Gly Thr Gly Met
1               5                   10                  15

Phe

<210> SEQ ID NO 3
<211> LENGTH: 19
<212> TYPE: PRT
<213> ORGANISM: Homo sapiens

<400> SEQUENCE: 3

Ser Gly Ser Val Ile Asp Gln Ser Arg Val Leu Asn Leu Gly Pro Ile
1               5                   10                  15

Thr Arg Lys

<210> SEQ ID NO 4
<211> LENGTH: 31
<212> TYPE: PRT
<213> ORGANISM: Homo sapiens

<400> SEQUENCE: 4

Met Val Ser Ala Leu Asn Ile Arg Val Gly Gly Thr Gly Met Phe Thr
1               5                   10                  15

Val Arg Met Ala Leu Phe Gln Thr Pro Ser Tyr Thr Gln Pro Tyr
                20                  25                  30

<210> SEQ ID NO 5
<211> LENGTH: 9
<212> TYPE: PRT
<213> ORGANISM: Homo sapiens

<400> SEQUENCE: 5

Leu Asn Leu Gly Pro Ile Thr Arg Lys
1               5

<210> SEQ ID NO 6
<211> LENGTH: 17
<212> TYPE: PRT
<213> ORGANISM: Homo sapiens

<400> SEQUENCE: 6

Gly Ser Val Ile Asp Gln Ser Arg Val Leu Asn Leu Gly Pro Ile Thr
1               5                   10                  15

Arg

<210> SEQ ID NO 7
<211> LENGTH: 18
<212> TYPE: PRT
<213> ORGANISM: Homo sapiens

<400> SEQUENCE: 7

Ser Gly Ser Val Ile Asp Gln Ser Arg Val Leu Asn Leu Gly Pro Ile

```
1               5              10              15

Thr Arg

<210> SEQ ID NO 8
<211> LENGTH: 27
<212> TYPE: PRT
<213> ORGANISM: Homo sapiens

<400> SEQUENCE: 8

Asp Leu Ile Ala Thr Met Met Pro Pro Ile Ser Pro Ala Pro Ile Gln
1               5                  10                  15

Ser Asp Asp Asp Trp Ile Pro Asp Ile Gln Ile
            20                  25

<210> SEQ ID NO 9
<211> LENGTH: 34
<212> TYPE: PRT
<213> ORGANISM: Homo sapiens

<400> SEQUENCE: 9

Gln Val Val Ala Gly Lys Lys Tyr Phe Ile Asp Phe Val Ala Arg Glu
1               5                  10                  15

Thr Thr Cys Ser Lys Glu Ser Asn Glu Glu Leu Thr Glu Ser Cys Glu
            20                  25                  30

Thr Lys

<210> SEQ ID NO 10
<211> LENGTH: 10
<212> TYPE: PRT
<213> ORGANISM: Homo sapiens

<400> SEQUENCE: 10

Lys Arg Pro Pro Gly Phe Ser Pro Phe Arg
1               5                  10
```

HEALTHY KIDNEY BIOMARKERS

FIELD OF THE INVENTION

The present invention relates to urinary biomarkers for healthy renal physiological performance of a native or a grafted kidney.

BACKGROUND OF THE INVENTION

The search for sensitive urinary biomarkers of kidney performance has attracted important efforts due to their potential value as clinical tools for detecting early signs of various diseases. The recent burst of powerful proteomic techniques such as ESi-MS, DESI-MS, MALDI-TOF-MS, SELDI-TOF-MS, DIOS-MS or LC-MS that allow sample screening across a statistically meaningful patient population, has led to the discovery and identification of distinctive urinary biomarkers of kidney dysfunction (Dihazi et al., Expert Rev Proteomics. 2007 February; 4(1):39-50)

In clinical nephrology, successful management of transplantation patients requires early detection and implementation of the most appropriate therapy. Available diagnostic methods include biochemical parameters and biopsies but the only non-invasive biomarker of allograft dysfunction is the insensitive, non-specific creatinine which does not allow detection of fibrosing changes at an early stage.

Research efforts have focused on urinary biomarkers of disease. A classical urinary proteome study reported that an unbiased proteomic approach can detect urine protein peaks associated with acute tubulointerstitial renal allograft rejection. Identification of these protein peaks by mass spectrometry demonstrated that they all derive from cleaved forms of beta2-microglobulin, presumably reflective of damaged renal proximal tubule cells (Schaub et al., 2005. *Am. J. Transplant.* 5, 729-738). Many studies followed this trend, to name a few: Dihazi et Al., Clin Chem. 2007 September; 53(9):1636-45; O'valle et Al., Transplant Proc. 2007 September; 39(7):2099-101; Peng et al., J Int Med Res. 2007 July-August; 35(4):442-9; WO-07121922-A2 and WO-07104537-A2). The number of published urinary biomarker studies is increasing rapidly. Most studies have looked at the soluble urine protein fraction, focusing on the identification of potential biomarkers in renal disease and diseases of the urogenital tract. They include studies of acute kidney injury, acute renal allograft rejection, glomerular disease and carcinoma of the kidney, bladder and prostate. In many cases the reported biomarkers remain unidentified, although some studies have identified a few biomarker proteins (O'Riordan et al., Am J Transplant 2007; 7:930-40; Schaub et al., 2005. *Am. J. Transplant.* 5, 729-738).

Notwithstanding these efforts, at the moment, standards for healthy renal function have not been the subject of any study. Traditionally, healthy renal function is assumed when a patient shows no signs of disease or pain. Monitoring healthy renal function may help identifying disorders at an early stage but, most importantly, it would provide clinicians with a powerful tool for managing patients with a grafted kidney.

A few urinary proteins that are present in samples of individuals with healthy kidney function but undergo a sharp reduction in disease, are known. The most prominent example is the Tamm-Horsfall glycoprotein (TH protein), also known as uromodulin (Kidney International, Vol. 16 (1979), pp. 279-289; JBC Vol. 265, No. 34, December 5, pp. 20764-20789, 1990). The TH protein is generally the most abundant protein in urine, and its presence can interfere with the detection of other proteins if it is not removed (Pisitkun et al., 2004. Proc. Natl. Acad. Sci. U.S.A. 101, 13368-13373). It can be depolymerised by use of reducing agents and warming. Human TH protein forms high molecular weight aggregates and may be dissociated into smaller molecular weight subunits of approximately 100 kDa by several agents (Stevenson et al., Biochem J 116:791-796, 1970). Thus, it is a common use in the field of urinary biomarker discovery to free the urine samples from uromodulin because it has no attributed diagnosing value. Uromodulin has, however, attracted certain interest because of its anti-inflammatory properties. The Japanese patent application JP-2002125673-A discloses a new uromodulin human gene and its uses as anti-inflammatory agent.

Other abundant urinary proteins are kinins. Mindroiu et al. (J Biol Chem. 1986 Jun. 5; 261(16):7407-11) compared the types of kinins excreted in fresh urine of dogs, rats, and humans using high performance liquid chromatography. They found that in human urine, the content of kinins was roughly 12% bradykinin, 30% Lys-bradykinin, 2% des-Arg1-bradykinin, and 41% of a then unknown kinin which was identical to Lys-Bradykinin but had an alanine in position 4 instead of a proline. Human urinary kallikrein incubated with semipurified human low molecular weight kininogen released 76% of the total kinins as Lys-bradykinin, 7% as bradykinin, and 17% as [Ala3]Lys-bradykinin. Thus lys-bradykinin is the most abundant type of kinin in urine, however, and despite its application in cardiovascular pathophysiology, no diagnostic value for renal pathophysiology has derived from its presence in urine.

A standard that positively asserts the fitness of a grafted kidney function would be of great value for clinicians in detecting early, otherwise undetectable, fibrosing changes.

Taking advantage of novel LC-MS techniques and owing to their innovative strategy for urinary biomarker discovery, the inventors have identified novel natural urinary peptides. All of them show reduced urinary concentrations in disease which qualify them as biomarkers of healthy kidney performance. Therefore, the present invention provides the physician with a clinical tool for diagnosing, instead of assuming, healthy renal physiology.

SUMMARY OF THE INVENTION

The invention relates to urinary biomarkers of healthy renal physiology. Thus, the invention provides a biomedical tool for monitoring healthy renal function.

Accordingly, one aspect of the invention comprises isolated urinary peptides selected from the group comprising SEQ ID NO:1 to 9 and combinations thereof for use as a physiological biomarker of healthy renal function.

In another aspect, the invention comprises the use of the isolated urinary peptide comprising SEQ ID NO: 10 as a physiological biomarker of healthy renal function.

The renal function comprises the function of a grafted kidney. The use comprises use in the prognosis and/or diagnosis of a nephropathy which comprises chronic allograft nephropathy.

In another aspect, the invention provides a method for monitoring, prognosing and diagnosing kidney physiology comprising a) collecting a sample of a body fluid from a subject. b) adding an internal standard for accurate quantization. c) concentrating and de-salting the sample collected. d) analyzing peptide content by proteomic techniques. e) quantifying content of peptides comprising SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10 and combinations thereof. f) comparing values obtained in step e) to control values. g) applying the comparative values gathered in step f) in the evaluation or diagnosis of the physiological performance of a kidney.

The sample comprises urine. The subject comprises patients of renal transplantation therapy. The internal standard comprises an isotopically labelled peptide with the same sequence as the analyte peptide but incorporating stable isotopes of carbon, nitrogen and hydrogen. The proteomic technique comprises ESI-MS, DESI-MS, DIOS-MS, SELDI-MS, MALDI-MS, LC/MS, tandem LC-MS/MS and any other high throughput mass spectrometry-based technique and/or antibody-based techniques including ELISA, protein/peptide arrays, antibody arrays or combinations thereof.

Another aspect of the present invention comprises the use of the method for monitoring, prognosing and diagnosing kidney physiology in the monitoring of the therapeutic efficacy of the treatment of a patient of a renal pathology.

A last aspect of the invention comprises a kit for in vitro diagnosing of a nephropathy in a sample of a body fluid of an individual comprising: at least one molecule capable of binding and/or recognizing at least one peptide of the group comprising SEQ ID: 1-10.

The sample comprises urine. The binding molecule comprises antibodies optionally in a labelled form or linked to an enzyme. The antibody may be fixed to a solid support

BRIEF DESCRIPTION OF THE DRAWINGS

FIG. 2. Unsupervised hierarchical clustering analysis classifies individual patients according to their underplaying pathological phenotype. The figure shows hierarchical clustering trees based on quantitative urinary polypeptide data from CAD subtypes (CAAR and IF/TA) and control specimens (SRT and cont) considering (A) the whole data set and (B) the less variable 500 molecular ions.

DETAILED DESCRIPTION OF EMBODIMENTS

Figure 1A:
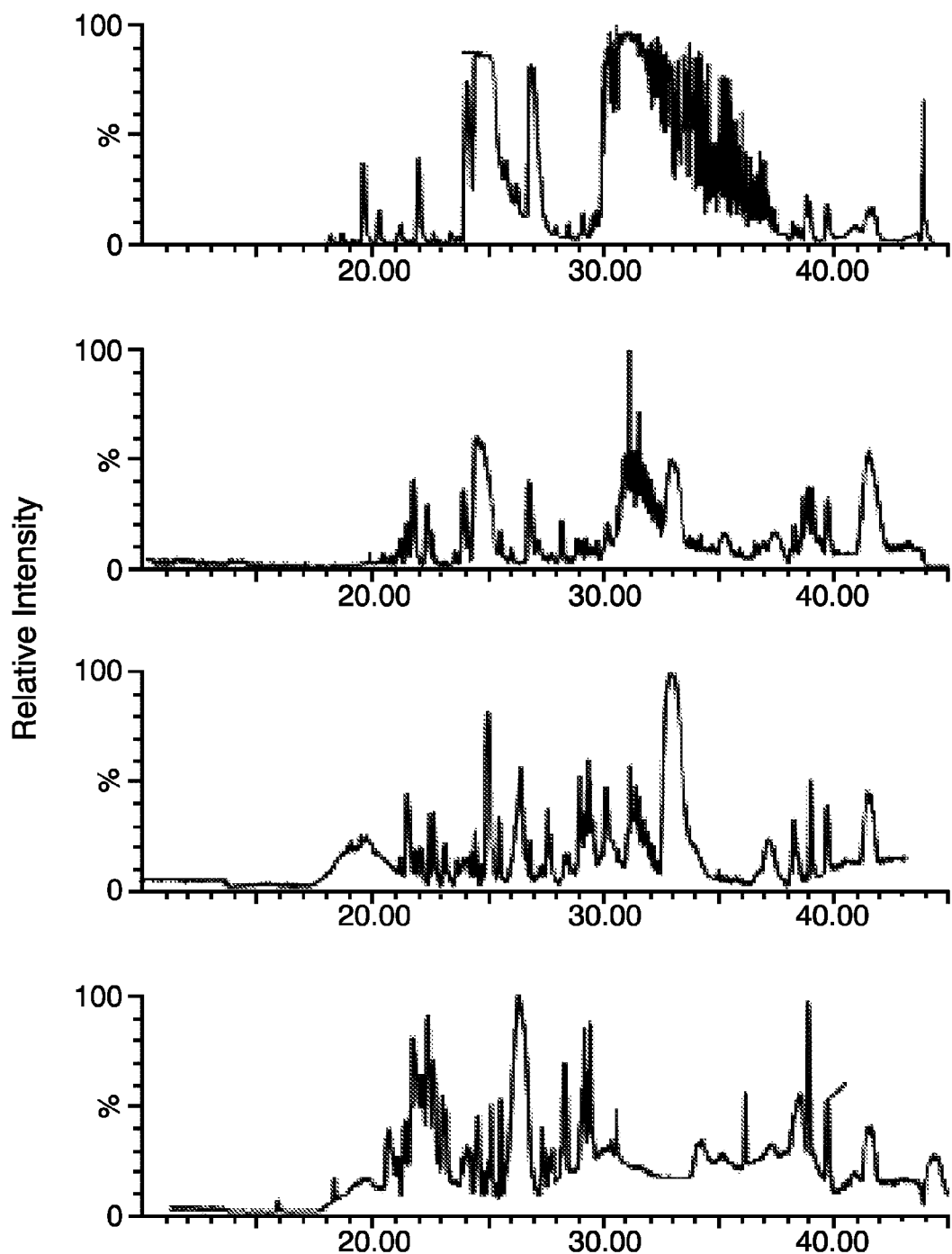
FIG. 1. Label-free quantitative strategy for the identification of urinary biomarkers of CAD. (A) Representative base peak ion chromatograms and (B) representative extracted ion chromatogram (XIC) of an ion at m/z 642.6 across the indicated sample group.

The present invention results from cooperative efforts in clinical proteonomics to identify novel urinary biomarkers that assist clinicians in the diagnosis of a disease and give directions as to which therapy may be more appropriate for the patient.

Inventors designed an innovative label-free strategy based on novel LC-MS techniques for quantitative proteonomics. This strategy, specific for biomarker discovery, allowed comparison of an unlimited number of samples thus obtaining statistically valid results (FIG. 1). From the analysis of urinary samples in a cohort of 32 individuals, inventors identified 9 novel naturally-occurring urinary peptides that qualify as biomarkers of healthy kidney performance because their presence is distinctively reduced in individuals whose biopsies reflected interstitial fibrosis and tubular atrophy but did not show changes in creatinine nor in the glomerular filtration rate or, otherwise, evidence of any specific etiology. Table 1 displays the clinical parameters of the study cohorts including control groups. FIG. 1B displays a representative example for a urinary biomarker in different stages of disease. Therefore, a first aspect of the present invention comprises 9 novel peptide biomarkers isolated from human urine. The sequences of said biomarkers correspond to SEQ. ID NO 1-9 disclosed herein.

In the context of the present invention, the term "isolated peptide" refers to a peptide contained in a bodily solution that has been separated from the human body; especially a peptide in excretory fluids such as urine.

In the course of their study, the inventors identified some of these peptides as fractions of both the human TH protein and kininogen. However, no evidence of the existence of these naturally-occurring peptide derivatives had been previously shown. Furthermore, full-length proteins have no attributed clinical or diagnosing value in nephrology.

TABLE 1 clinical parameters of the study cohorts and control groups.
Mean ± SD

|  | CAD | | Control | |
|---|---|---|---|---|
|  | IF/TA Group | CAAR Group | Stable renal transplant recipients | Healthy controls |
| Sample number (n) | 8 | 10 | 5 | 9 |
| Age (y) | 51 ± 10.69 | 47.22 ± 17.07* | 36.2 ± 8 | 43 ± 10 |
| Creatinine (mg/dl) | 3.2 ± 1.68 | 2.98 ± 1.64* | 1.08 ± 0.3 | 0.91 ± 0.3 |
| Proteinuria (g/24 h) | 2.67 ± 2.90 | 3.11 ± 3.33* | 0.20 ± 0.05 | 0.11 ± 0.02 |
| GFR (ml/min/ 1.73 m2) | 28.88 ± 17.65 | 33.44 ± 12.05* | 82.22 ± 4 | 110 ± 10 |

*T Test NS between IF/TA vs CAAR groups. IFTA = interstitial fibrosis and tubular atrophy with no other etiology; CAAR = chronic active antibody-mediated rejection. GFR = Glomerular filtration rate from serum creatinine estimate by Modification of Diet in Renal Disease (MDRD) Study equation.

As an exception, urinary peptide comprising SEQ ID NO 10 had been previously identified and corresponds to Lys-bradykinin. It finds clinical application as a biomarker for hypertension and in the development and progression of cardiovascular disease and cancer. Surprisingly, as demonstrated by the inventors, this peptide has a novel clinical application as a physiological biomarker of healthy renal function.

Hence, the single inventive concept of the invention described in the present application comprises "Healthy Kidney Biomarkers", some of which are novel entirely; other which is novel in its industrial application. Accordingly, another aspect of the present invention comprises the use of an isolated urinary peptide comprising SEQ ID NO: 10 as a physiological biomarker of healthy renal function.

Because monitoring of function fitness is of particular clinical interest in patients with a grafted kidney, another aspect of the present invention comprises the use of any of the isolated urinary peptides from the group comprising SEQ ID NO: 1-10 or combinations thereof as biomarkers in monitoring renal function of a kidney allograft.

In order to better assist a physician in reaching a diagnosis or in deciding a personalized, better suited, therapy, another aspect of the present invention comprises the use of the isolated urinary peptides from the group comprising SEQ ID NO: 1-10 or combinations thereof in the prognosis and/or diagnosis of a nephropathy. Specially, when the nephropathy is Chronic Allograft Nephropathy.

Figure 3A:
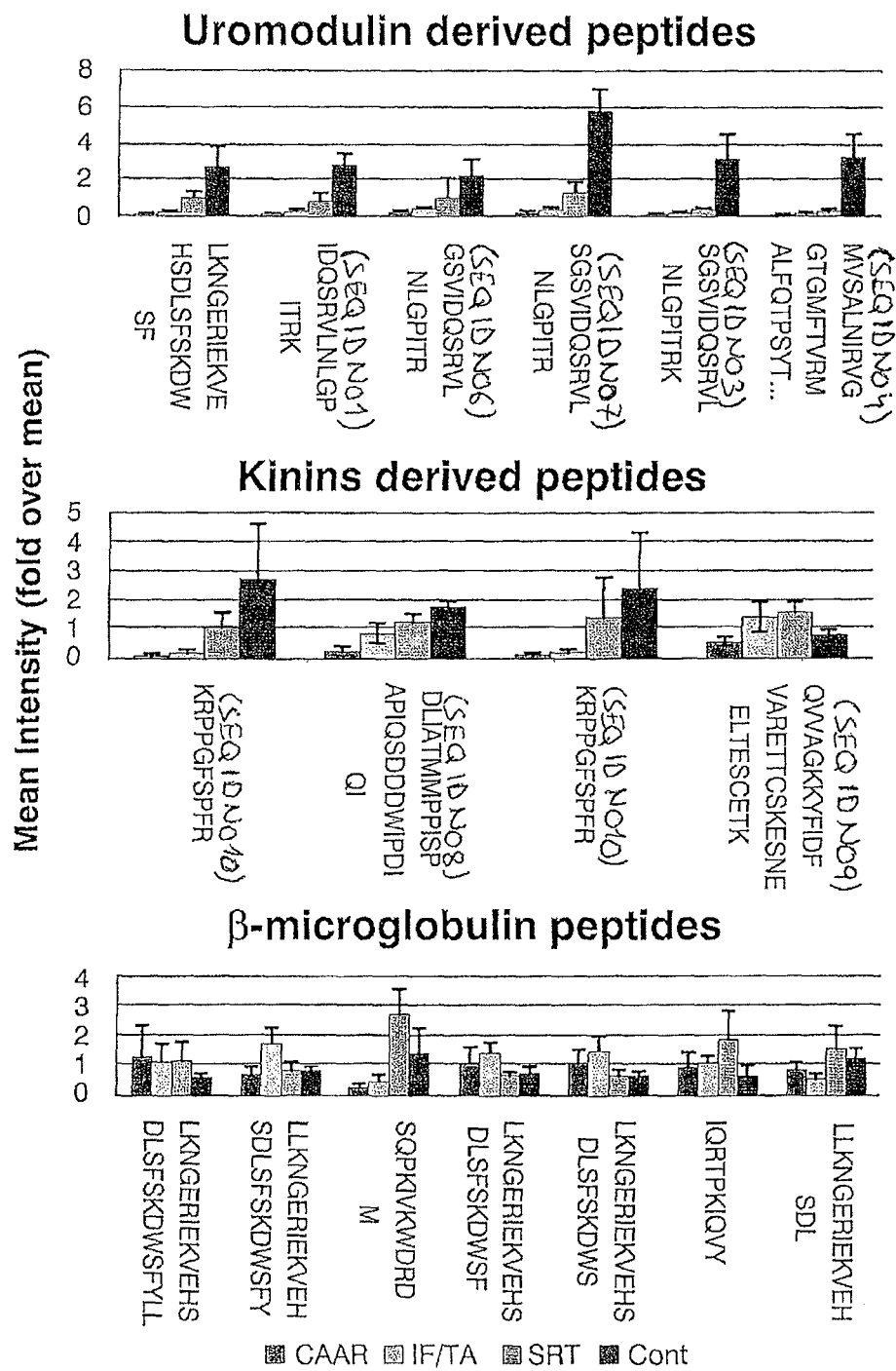
FIG. 3. Specific peptides derived from uromodulin and kinin are biomarkers for the diagnosis of CAD. (A) Ionic intensities of the peptides shown correspond to the mean values within a sample group. Values represent mean±SD. (B) Intensities shown correspond to the mean of the all the peptides derived from a single protein within individual patients. Values represent mean±SD.
Figure 3B:
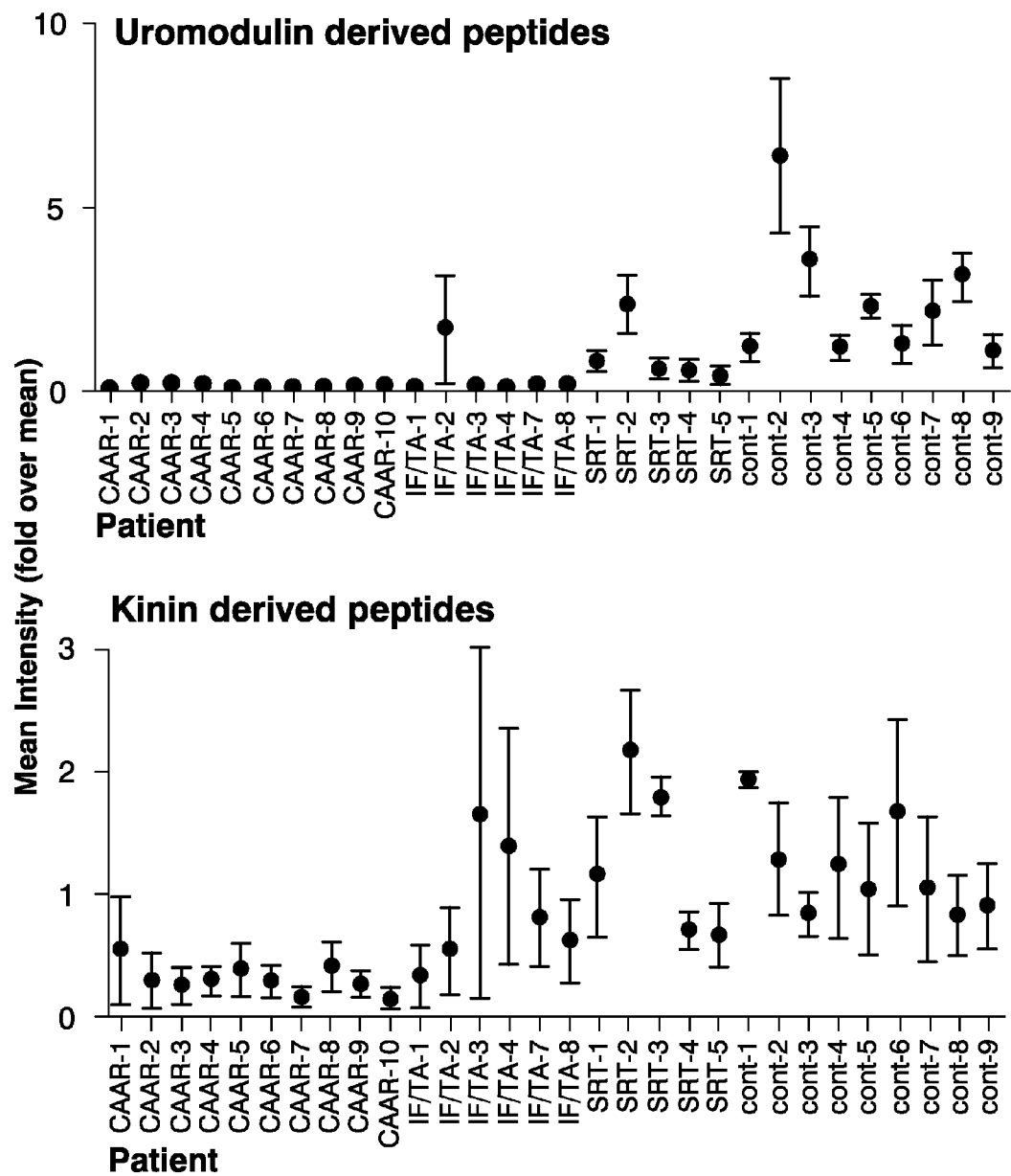

FIG. 3A (top panel) shows that peptides derived from uromodulin are significantly more abundant in control patients than in the other groups (control versus chronic active antibody-mediated rejection (CAAR), p<0.0001). Of the peptides derived from kininogen, bradykinin peptides (with two different charge states) were more abundant in Stable Renal Transplant (SRT) and control than in Chronic Allograft Dysfunction (CAD) patients (FIG. 3, middle panel). Examination of expression of specific peptides from uromodulin and kinins in individual patients revealed that uromodulin peptides were consistently more abundant in control and SRT than in CAD groups (FIG. 3B). A greater sensitivity was achieved by considering the mean intensity of all the peptides derived from uromodulin. Indeed this value could correctly identify 94% (17/18) of all CAD patients with 100% specificity (none of the control group had low levels of uromodulin peptides, FIG. 3B). Thus a combination of biomarkers had more discriminatory power than any of the single biomarkers we identified and this fact argues that using the mixture of biomarkers identified here would increase the specificity and sensitivity of early CAD diagnosis.

Thus, according to the present invention, peptides derived from uromodulin and bradykinin are specific biomarkers of a healthy kidney, whose presence could be used to discriminate CAD patients and unaffected individuals.

It would be desirable to provide a clinical protocol for monitoring patients in nephrology according to the use of healthy kidney biomarkers of the present invention. Therefore, another aspect of the invention comprises a method for monitoring kidney physiology comprising a) collecting a sample of a body fluid from a subject; b) Adding an internal standard for accurate quantization.

c) Concentrating and de-salting the sample collected; d) analyzing peptide content by proteomic techniques; e) quantifying content of peptides selected from the group comprising SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10 and combinations thereof; f) comparing values obtained in step d) with control values; g) applying the comparative values gathered in step e) in the evaluation or diagnosis of the physiological performance of the kidney.

To make the technique quantitative the method includes the addition of an internal standard after collecting the sample and prior to performing any of the steps. In a preferred embodiment, internal standard is an isotopically labelled peptide with the same sequence as the analyte peptide to be quantified but incorporating stable isotopes of carbon, nitrogen and hydrogen. These isotopes are not radioactive, but allow for accurate quantification in absolute units (eg. mol/l or mg/ml) to serve in its clinical application.

The method of the present invention is especially appropriate for use in a non-invasive patient monitoring protocol. Consequently, a preferred embodiment of the invention comprises the method described herein, wherein the body fluid sample is urine. Additionally, the method of the present invention is particularly useful in the field of renal transplantation. Accordingly, another preferred embodiment comprises the method described herein, wherein the subject is a patient of renal transplantation therapy.

Once the peptides of the present invention have been identified in urine, several proteomic techniques may be applied in performing the method of the present invention. Hence, a preferred embodiment of the invention comprises a method comprising proteomic techniques chosen from the group comprising ESI-MS, DESI-MS, DIOS-MS, SELDI-MS, MALDI-MS, LC/MS, tandem LC-MS/MS and any other high throughput mass spectrometry-based technique and/or antibody-based techniques including ELISA, protein/peptide arrays, antibody arrays or combinations thereof.

Patients that have suffered kidney transplantation receive a constant immunosuppressive therapy supplemented at times with other specific substances for aiding and improving allograft fitness. Often, after-transplantation therapies ought to be reviewed and personalized for individual patients. In helping clinicians deciding a better fitted therapy, a preferred embodiment of the method of the present invention comprises its use in the monitoring of the therapeutic efficacy of the treatment of an individual.

A quick and readily applicable method would be desirable in the continued monitoring of a patient's renal function. Accordingly, an aspect of the present invention comprises a Kit for in vitro diagnosing of a nephropathy in a sample of a body fluid of an individual comprising at least one molecule capable of binding and/or recognizing at least one peptide of the group comprising SEQ ID 1-10.

A preferred embodiment of the invention comprises a kit wherein the sample used is urine and the binding molecule is an antibody, optionally labelled or linked to an enzyme. Such embodiment may further comprise a substantial component including a solid support wherein an antibody capable of binding and recognizing a sequence selected from the group consisting of SEQ ID NO: 1-10 and combinations thereof is attached or affixed to said solid support. In some embodiments, the solid support is a test strip suitable for dipping into a solution of urine.

In addition, the kit of the present invention may include detection reagents, buffers or devices. In preferred embodiments, the kit contains all necessary elements to perform a detection assay. Including all controls, directions for performing assays, and necessary hardware or software for analysis and presentation of results.

In some embodiments, the kits contain an assay in a test strip format. Kits may be designed for use in a clinical setting, a laboratory setting or in a patient's home setting.

Example 1

Study Cohorts

Thirty-two individuals were included in the present study: 18 patients with clinical and histopathological characterization of CAD and 14 controls. The patients fell into two groups: 1) eight patients (five men and three women) with interstitial fibrosis and tubular atrophy (IF/TA) and no evidence of any specific etiology (IF/TA group); 2) 10 patients (seven men and three women) with Chronic active antibody mediated rejection (CAAR) defined by morphological features including transplant glomerulopathy (TG) and IF/TA with or without peritubular capillary loss, and fibrous intimal thickening in arteries without duplication of the internal elastica, diffuse C4d deposition in peritubular capillaries and the presence of donor specific antibody (CAAR group).

All transplant recipients received immunosuppressive treatment with a calcineurin inhibitor, mycophenolate mofetil, and prednisone. There were no significant differences between the IF/TA and CAAR groups with respect to age, gender, diabetes duration, arterial blood pressure, body mass index, and GFR (Table 1) but they were classified into these CAD subgroups according to histopathological criteria (Table 2).

The controls fell into two groups: 1) stable renal transplant recipients: five live-donor recipients of a first renal graft following immunosuppressive treatment with tacrolimus, mycophenolate mofetil, and prednisone; and 2) healthy controls: 9 volunteers with normal blood pressure (systolic blood pressure<130 mmHg and diastolic blood pressure<80 mmHg), and no history of diabetes mellitus, ischemic heart disease, stroke or peripheral vascular disease. Table 1 shows the baseline characteristic of patients with CAD and controls.

The study was approved by the institutional review board at the Hospital Clinic in Barcelona, and both patients and controls gave informed consent for the collection and analysis of their urine.

Histopathology

Transplant biopsies consisted of two cores obtained with 18-gauge needles using ultrasound guidance because of clinical indication. Paraffin sections were prepared and stained with hematoxylin-eosin, trichrome, periodic acid-Schiff and periodic acid-Schiff-methenamine silver. The biopsies were analyzed and were scored according to the Banff classification by a pathologist who was blinded to the results of molecular studies (27). TG was diagnosed by light microscopy based on double contours of glomerular basement membranes (GBM) (28) and was supported by immunofluorescence studies, which showed mesangial IgM and/or C3 or negative immunofluorescence findings. Peritubular capillaritis in TG biopsies was graded according to the quantitative criteria of the last Banff update (27). C4d staining was done in all biopsies using frozen tissue. Murine monoclonal anti-human C4d 100 IL (Quidel Corporation, San Diego, Calif.), followed by fluorescent antisera (CyTM2-conjugated AffiniPure Goat Antimouse IgG, Jackson ImmunoResearch Laboratories, Inc, West Grove, Pa.) were added to the frozen sections.

There was no evidence of CAAR or transplant glomerulopathy (TG), and C4d was negative in all patients with pure IF/TA. Mean glomerular double contour (CG) score was 1.89, and C4d was positive in all patients in the CAAR group. Evidence of chronic active T-cell-mediated rejection was excluded in all samples from this group. Table 2 summarizes Banff scores in the IF/TA and CAAR groups.

Sample Preparation and Purification

Fifty milliliters of early morning urine were collected immediately prior to renal biopsy. Protease inhibitor cocktail (Complete Mini, Roche, Mannheim, Germany) was added and specimens were rapidly frozen in dry ice and stored at −80° C. until analyzed. Urine samples were concentrated and separated from inorganic salts by solid phase extraction using a reversed phase HLB Oasis 94226 (Waters, Milford, Mass.) as the stationary phase essentially as described (12) with minor modifications. Briefly, cartridges were conditioned with 10 ml of 100% acetonitrile (ACN) and equilibrated with 10 ml 0.1% trifluoroacetic acid (TFA)/5% ACN. After loading 1 ml of sample (acidified with 0.1% TFA at pH 3 and a final concentration of 5% ACN), the cartridge bed was washed with 10 ml 0.1% TFA/5% ACN and peptides were subsequently eluted with 2 ml 0.1% TFA/60% ACN. Separation from organic salts was by strong cation exchange (SCX) using magnetic beads (Dyna beads, Invitrogen) as follows. Beads were conditioned with 1M NaCl/50 mM ammonium bicarbonate pH 8.8 and equilibrated with loading solution (0.1% TFA/20% ACN). After application of the sample from the reversed phase step, bound peptides were washed 3 times with loading solution. Elution was with 500 mM ammonium acetate in 20% ACN. Eluted peptides were dried in a Speed-Vac and stored at −80° C.

Mass Spectrometry

Dry peptides were dissolved in 10 □l of 0.1% TFA/2% ACN and 10% of this solution analyzed in a LC-MS/MS system that consisted of a nanoflow ultrahigh pressure liquid chromatograph (Acquity, Waters/Micromass) connected on line with a Q-TOF Premier mass spectrometer (Waters/Micromass) equipped with a nanoESI ion source. Separations were performed in a BEH 100 µm×100 mm column (Waters/Micromass) at 400 µL/min flow rate with an operating back pressure of about 3,000 psi. Gradient runs were from 2% B to 30% B in 30 minutes followed by a 5 minute wash at 80% B and a 7 minute equilibration step at 2% B. Solvent A was 0.1% formic acid in LC-MS grade water (Optigrade, LGC, UK) and solvent B was 0.1% formic acid in LC-MS grade ACN (Optigrade, LGC, UK). For LC-MS/MS experiments, survey MS scans of 500 ms were followed by 3 MS/MS scans (500 ms each), which were triggered in data-dependent mode when multiply charged ions in the MS survey scans were above 15 counts/s. LC-MS analyses were performed by acquiring survey 1 s scans (no MS/MS functions) but with otherwise the same LC and MS parameters as for the LC-MS/MS experiments.

Data Analysis

Quantification.

Lists of ions selected for MS/MS were fed into PESCAL, a program written in house for the automation of label-free LC-MS data analysis (4). PESCAL then used the m/z and retention time (tR) of the ions detected to construct extracted ion chromatograms (XICs) across the LC-MS runs of individual urine samples. Windows for XIC construction were 25 ppm and 2 minutes for m/z and tR, respectively. The intensity values (peak areas and heights) of these XICs were parsed into Excel files for normalization and statistical manipulation and analysis. Peak intensity values were normalized to the mean intensities of all peaks within a sample and then to the mean of the individual peptide ion across samples.

Statistical Analyses.

For unsupervised clustering analysis, normalized ion intensity values were log converted and fed into Cluster (Eisein software, (29) for clustering and TreeView (Eisein software) for visualization of the clustering results.

The non-parametric Mann-Whitney test was used to infer the statistical significance of the LC-MS results. These analyses were performed using a commercial statistical package (Prism).

Statistical significance of clinical chemistry tests was inferred by the student T-test. Relative levels of polypeptide ions were also analyzed using discriminant analysis (Systat, version 10.2, Richmond, Calif., USA) to identify combinations of these polypeptides that best discriminate between disease states. A logistic regression model was also built using the same polypeptide ions to calculate prediction scores for each sample, allowing us to construct a receiver operating characteristic (ROC) curve based on these values (30).

MS/MS Data Analysis.

The identity of a subset of peptides detected was determined by searching MS/MS spectra against the International Protein Index (IPI) Human database (version 3v.44) using the MASCOT search engine. Searches were restricted to 50 ppm and 100 ppm for parent and fragment ions, respectively. No enzyme restriction was selected. Hits were considered significant when they were above the statistical significant threshold (as returned by MASCOT) and at least two peptides matched a protein entry.

Results

Patients

We aimed at identifying urinary peptides that could serve as biomarkers of CAD. For this, 14 controls and 18 specimens with well defined clinical features were included in this study (Table 1). As described in more detail above, histopathological parameters classified the patient group into two subgroups: IF/TA and CAAR (Table 2).

Analytical Strategy

In order to increase the probabilities of identifying useful biomarkers of CAD, we aimed at quantifying urinary peptides across samples as comprehensively and accurately as possible. For this, we used an analytical strategy that consists of using the elution profiles of individual peptide ions in LC-MS runs that had been previously detected in LC-MS/MS experiments. This is therefore a targeted quantification strategy because we only quantified (by LC-MS) those ions that had been previously detected (although not necessary identified) in urine by data-dependent LC-MS/MS. In order to generate a list of quantifiable urinary peptides, we pooled undigested urinary peptides from the same patient group and analyzed them by LC-MS/MS. These analyses were performed in triplicate (three times per sample group), with each replicate LC-MS/MS experiment including the list of peptides identified in the previous LC-MS/MS runs as exclusion lists, as reported before. These experiments resulted in the selection of 6250 multiply charged ions for MS/MS. It should be noted that this was an unfiltered list and many of these ions were detected in more than one sample pool. Quantification was performed from LC-MS data of individual samples (without pooling) by targeted quantification of the 6250 ions that had been selected for quantification by data-dependent LC-MS/MS.

Figure 1B:
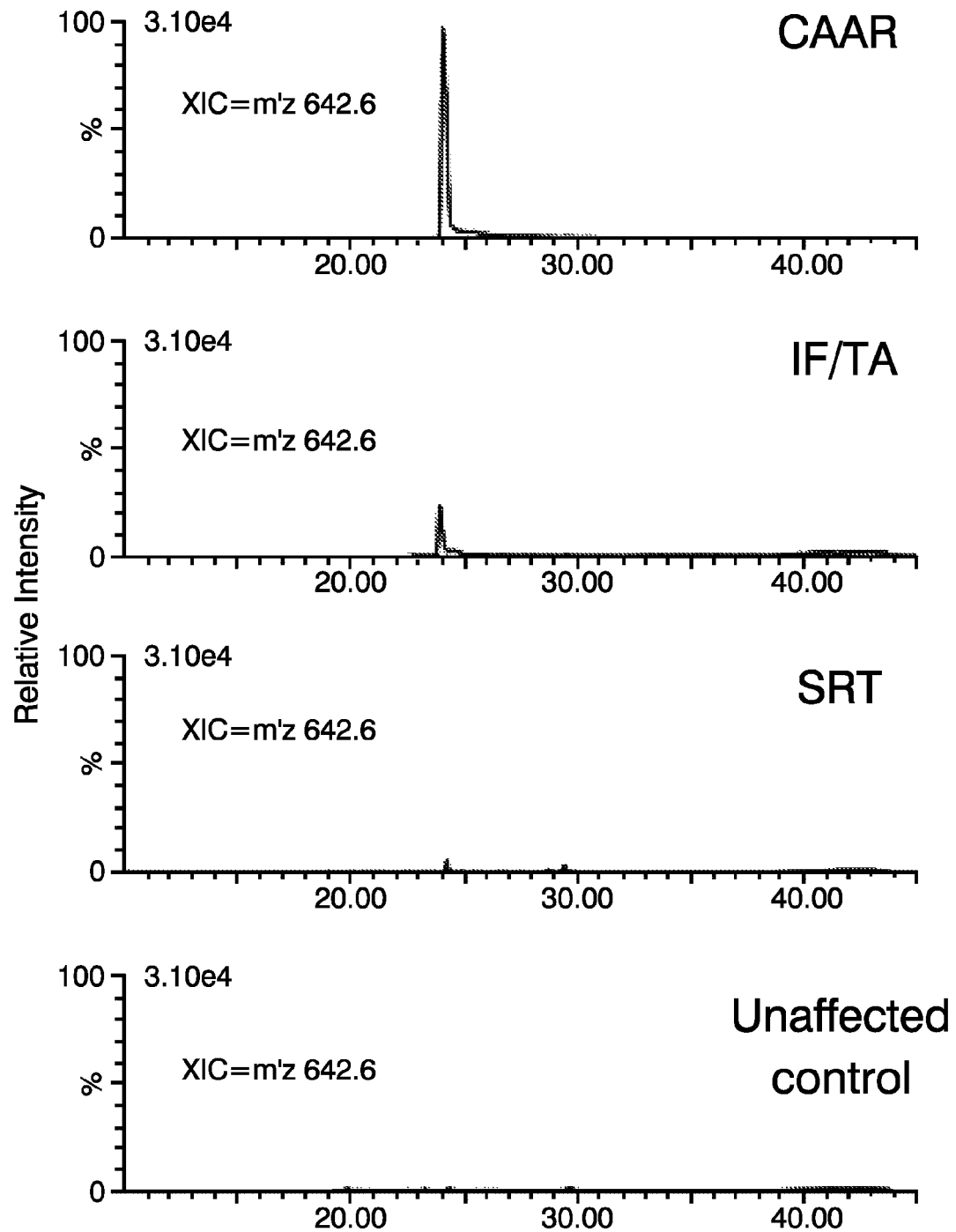

To exemplify how this analytical strategy works, FIG. 1A shows representative LC-MS ion chromatograms of peptides extracted from the urine of IFTA, CAAR, SRT, and control donors. Each of the peaks in these chromatograms was formed by the elution of several polypeptides and therefore, by themselves, they cannot be used to quantify individual peptides. For quantification, we calculated the area under the curve of a chromatogram obtained from the elution profile of each individual peptide (i.e., and extracted ion chromatogram, XIC), an example of which is shown in FIG. 1B. In order to make this approach practical, we used an in-house computer program to automate the creation of these XICs. The program also calculates their intensities (4). In the illustrative example shown in FIG. 1B, a molecular ion at m/z 642.6 was present with about 5 fold enrichment in CAAR urine, compared with IFTA and at least 15 fold when compared with SRT and control samples (FIG. 1B).

Hierarchical Clustering of Label-Free Quantitative LC-MS Data Classify Urinary Peptidomes According to their Underlying Pathological Phenotype As mentioned above, using this strategy we identified ~6250 ions in our analyses before filtering and about 2300 after deleting duplicates; and for all of them we obtained XICs and calculated their intensities across 14 controls and 18 CAD specimens. FIG. 2A shows that it was possible to separate control and CAAR patients based on unsupervised hierarchical clustering using the intensities of all the identified peptides, with SRT and IFTA showing some overlapping. Filtering of the data to include the 500 less variable peptide ions resulted in a similar clustering pattern (compare FIGS. 2B and 2C), but SRT and control were completely separated from CAAR in the analysis shown in FIG. 2B (only 500 peptides considered), whereas one SRT patient was placed in the CAAR/IFTA cluster when all the peptide ions were included in the analysis (FIG. 2A). Further filtering to include lower number of peptides for hierarchical clustering gave similar results as in FIG. 2B (data not shown). These results indicate that the polypeptide composition in the urine of CAD patients is significantly different from that of SRT and control subjects and that our label-free quantitative LC-MS strategy can detect these differences.

Identification of Specific Peptides Derived from Uromodulin and Kinins as Specific Biomarkers for the Diagnosis of CAD In order to characterize in more detail the molecular differences between these specimens, we compared the intensities of the subset of peptides across samples that could be identified by Mascot database searchers. FIG. 3A (top panel) shows that peptides derived from uromodulin were significantly more abundant in control patients than in the other groups (control versus CAAR, $p<0.0001$). Of the peptides derived from kininogen, bradykinin peptides (with two different charge states) were more abundant in SRT and control than in CAD patients (FIG. 3, middle panel). Examination of expression of specific peptides from uromodulin and kinins in individual patients revealed that uromodulin peptides were consistently more abundant in control and SRT than in CAD groups (FIG. 3B). The individual peptide ions that best discriminated between controls and CAD groups were those derived from uromodulin at m/z 638 and kininogen at m/z 1003, resulting in correct identification of 84% (14/18) of the control and CAD group patients. Logistic regression analysis resulted in selection of the same ions. A ROC curve constructed from the LR scores gave an area under the curve (AUC) value of 0.82.

A greater sensitivity was achieved by considering the mean intensity of all the peptides derived from uromodulin. Indeed this value could correctly identify 94% (17/18) of all CAD patients with 100% specificity (none of the control group had low levels of uromodulin peptides, FIG. 3B). Thus a combination of biomarkers had more discriminatory power than any of the single biomarkers we identified and this fact argues that using the mixture of biomarkers identified here would increase the specificity and sensitivity of CAD diagnosis.

Other peptides could be identified in these specimens, but they did not provide discriminatory information. As an example, FIG. 3A (bottom panel) shows that peptides derived from β-microglobulin were present at approximately the same amounts across the sample groups. Thus, our data indicate that peptides derived from uromodulin and bradykinins are specific biomarkers of a healthy kidney, whose presence could be used to discriminate CAD patients and unaffected individuals.

The peptides discussed above, although useful for the diagnosis of CAD, could not discriminate between CAAR and IFTA groups.

The invention claimed is:

1. A method for monitoring, prognosing or diagnosing a grafted kidney physiology in a patient of renal transplantation therapy comprising:
   a) Collecting a sample of a body fluid from a subject;
   b) Adding an internal standard for accurate quantization;
   c) Concentrating and de-salting the sample collected;
   d) Quantifying and analyzing the content of peptides selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10 by liquid chromatography (LC) followed by mass spectroscopy (MS);
   e) Comparing values obtained in step d) with control values; and
   f) Applying the comparative values gathered in step d) in the evaluation or diagnosis of the physiological performance of the kidney.

2. The method of claim 1 wherein the body fluid sample is urine.

3. The method of claim 1 wherein the internal standard is an isotopically labelled peptide with the same sequence as the analyte peptide but incorporating stable isotopes of carbon, nitrogen and hydrogen.

4. The method of claim 1 wherein MS comprises ESI-MS, DESI-MS, DIOS-MS, SELDI-MS, MALDI-MS.

* * * * *